United States Patent [19]  [11] 3,933,856
Khairullin et al.  [45] Jan. 20, 1976

[54] METHOD FOR PREPARING TETRAHYDROTHIOPHEN

[76] Inventors: Vazikh Kashapovich Khairullin, ulitsa Sibirsky trakt, 22, kv. 24; Margarita Alexandrovna Vasyanina, ulitsa 50 let Oktyabrya, 18, kv. 7, both of Kazan, U.S.S.R.

[22] Filed: Nov. 8, 1973

[21] Appl. No.: 413,950

[52] U.S. Cl.............................. 260/332.8; 260/329
[51] Int. Cl.² ....................................... C07D 333/10
[58] Field of Search .......... 260/329 R, 609 R, 332.8

[56] References Cited
FOREIGN PATENTS OR APPLICATIONS

| | | | |
|---|---|---|---|
| 672,496 | 10/1963 | Canada | 260/329 |
| 913,584 | 12/1962 | United Kingdom | 260/329 |

Primary Examiner—James O. Thomas, Jr.
Assistant Examiner—A. Siegel
Attorney, Agent, or Firm—Holman & Stern

[57] ABSTRACT

This invention relates to a method for preparing tetrahydrothiophen, consisting in that tetrahydrofuran is reacted with a sulphidation agent, elementary sulphur or phosphorus sulphides, with the stoichiometric ratio of the above-named substances, and at a temperature of 175°–215°C, with subsequent isolation of the end product. The interaction between tetrahydrofuran and elementary sulphur can be realized in the presence of a red phosphorus additive which increases the yield of the end product. In the described method a non-toxic and safe (with respect to explosion) sulphidation reagents is used which markedly improves the labour conditions. The method is simple, requires no complicated process equipment, and can be effected under milder conditions as compared with the known methods.

4 Claims, No Drawings

METHOD FOR PREPARING TETRAHYDROTHIOPHEN

The invention relates to methods for preparing tetrahydrothiophen used as an intermediate in synthesizing thiophen, tetramethylene sulphoxide, sulpholane, and 1,4-dihalogen butanes. The products manufactured from tetrahydrothiophen are used as additives for motor fuels, for the extraction of aromatic hydrocarbons from petroleum products, for preparing polysulphide elastomers, in medicine, and etc.

A method for preparing tetrahydrothiophen is known in the art which consists of the interaction between tetrahydrofuran and a sulphidation agent, namely hydrogen sulphide, in the vapour phase with a stoichiometric ratio of the said substances, and at a temperature of from 275°–450°C, in the presence of alumosilicate catalyst, and with the subsequent isolation of the end product.

The disadvantage of the known method is the use of poisonous and explosion-dangerous hydrogen sulphide which contaminates the environment and corrodes steel apparatus. Moreover, the use of a hydrogen-sulphide generator complicates the process flowsheet. The disadvantage of the known method resides also in the high temperature at which tetrahydrofuran reacts with the sulphidation agent.

The general object of the invention is to eliminate these disadvantages.

The specific object of the invention is to provide a method for preparing tetrahydrothiophen in which non-poisonous and non-explosive sulphidation agents can be used.

Another object of the invention is to provide a method for preparing tetrahydrothiophen in which the reaction between tetrahydrofuran and the sulphidation agent an be effected at lower temperature.

Still another object of the invention is to provide a process that an be realized with simple equipment.

In accordance with these and other objects, the invention consists in reacting tetrahydrofuran with the sulphidation agent, viz. elementary sulphur, or sulphides of phosphorus, taken in a stoichiometric ratio of the said substances, at a temperature of from 175°–213°C, and with subsequent the isolation of the end product.

The use of the new sulphidation agents in the proposed method, namely, of elementary sulphur and sulphides of phosphorus, improves the labour conditions (the said reagents are non-poisonous and non-explosive), and also requires lower process temperatures (175°–215°C). The said sulphidation agents provide favourable conditions for carrying out the process in steel apparatus. The simple flowsheet of the proposed process is another advantage of the invention.

In order to increase the yield of the end product it is recommendable to carry out the reaction between tetrahydrofuran and elementary sulphur in the presence of red phosphorus taken in a ratio of from 0.5–1 g-atom per g-mole of tetrahydrofuran.

For ensuring a higher tetrahydrothiophen yield, the reaction between tetrahydrofuran and the elementary sulphur in the presence of red phosphorus should be carried out at a temperature of from 180° to 200°C.

The proposed method for preparing tetrahydrothiophen can be realized as follows:

The reaction between tetrahydrofuran and the sulphidation agent is carried out in a rotating autoclave or in an autoclave provided with a stirrer. The autoclave is provided also with a pressure gauge, an electric heater, and a thermocouple connected to a potentiometer, which records and controls the process temperature. The stoichiometric quantities of the tetrahydrofuran and the sulphidation agent (elementary sulphur or phosphorus sulphides, for example $P_4S_3$, $P_2S_3$, $P_4S_7$, $P_2S_5$) are loaded into the autoclave (rotary, or with a stirrer). In order to increase the yield of the end product, the elementary sulphur can be introduced into the autoclave along with an additive of red phosphorus taken in a ratio of from 0.5–1 g-atom per g-mole of tetrahydrofuran. The autoclave is closed, and the reacting components are heated to the required temperature and kept at this temperature for the time required to accomplish the process. The completeness of the reaction is judged by establishing the constant pressure inside the autoclave. The heating is then discontinued, the autoclave contents are cooled to room temperature and the excess pressure is released. The autoclave is then opened, and the reaction mixture, which is a viscous brown liquid, is unloaded from the autoclave and the end product is isolated therefrom, for example, by extracting with organic solvents, or by distillation. In the latter case (which is preferred), the reaction mixture is placed into a still, and the end product is distilled at a temperature of 116°–122°C at atmospheric pressure. In order to increase the yield of tetrahydrothiophen, additional quantities of the product can be recovered from the still bottoms by extraction with organic solvents, for example, with carbon tetrachloride.

For a better understanding of the invention, the following examples of its practical embodiment are given by way of illustration.

EXAMPLE 1

A rotary autoclave of one liter capacity, provided with a pressure gauge and a heat control system (electric heater, thermocouple, potentiometer), was charged with 72 g (one g-mole) of tetrahydrofuran, 32 g (one g-atom) of crushed elementary sulphur, and the reaction mixture was kept at a temperature of 200°C for 18 hours (with rotation of the autoclave). The autoclave was then cooled to room temperature, the pressure was released, and the liquid reaction products of brown colour were transferred into a distillation flask. The result of the distillation yielded 17.1 g (23.2%) of unreacted tetrahydrofuran, having boiling point of 64°C (760 mm Hg), and 10.5 g (11.9%) of tetrahydrothiophen having a boiling point of from 118°–122°C (760 mm Hg), $d_4^{20}$ 1.000, $n_D^{20}$ 1.5010, which well agrees with the available data (b.p. 116°–122°C at 760 mm Hg, $d_4^{20}$ 1.000, $n_D^{20}$ 1.5010; E. E. Reid, Organic Chemistry of Bivalent Sulphur, vol. 3, N.Y. 1960, p. 90).

EXAMPLE 2

A rotary steel autoclave as described in Example 1, was charged with 72 g (one g-mole) of tetrahydrofuran, 32 g (one g-atom) of crushed sulphur, and 31 g (one g-atom) of red phosphorus, and the mixture was kept at 180°C for six hours with rotation of the autoclave. The autoclave was then cooled to room temperature, the pressure was released and a brown liquid product from the reaction was transferred into a distillation flash. The products of distillation were 34.5 g (37.7%) of tetrahydrothiophen having the boiling point of 118°–122°C (760 mm Hg), $d_4^{20}$ 1.000, $n_D^{20}$ 1.5010.

EXAMPLE 3

A rotary steel autoclave, as in Example 1, were charged with 144 g (2 g-moles) of tetrahydrofuran, 64 g (2 g-atoms) of crushed elementary sulphur and 62 g (2 g-atoms) of red phosphorus, and the mixture was kept at a temperature of 200°C for two hours. The autoclave was then cooled to room temperature and the pressure was released. The liquid reaction products were transferred into a distillation flask and 96 g (50.2%) of tetrahydrothiophen were isolated (b.p. 116°–122°C, at 760 mm Hg., $d_4^{20}$ 1.000, $n_D^{20}$ 1.5010).

EXAMPLE 4

A rotary steel autoclave, as in Example 1, was charged with 72 g (one g-mole) of tetrahydrofuran, 32 g (one g-atom) of crushed elementary sulphur, and 15.5 g (0.5 g-atom) of red phosphorus, and the mixture was kept at a temperature of 200°C for 36 hours. The autoclave was then cooled to room temperature and the pressure released. The liquid reaction products were transferred into a distillation flask to isolate 19.5 g (22.2 per cent) of tetrahydrothiophen having a boiling point 118°–122°C (760 mm Hg), $d_4^{20}$ 1.000, $n_D^{20}$ 1.5010.

EXAMPLE 5

A steel autoclave having a 0.5 liter capacity, provided with a stirrer, a pressure gauge and a heating control system (electric heater, thermocouple, potentiometer), was charged with 72 g (one g-mole) of tetrahydrofuran, 46 g (0.2 g-mole) of phosphorus sulphide $P_2S_5$, and the mixture was kept at a temperature of 195°C with stirring for six hours. The autoclave was then cooled to room temperature, the pressure was released and the liquid reaction products, brown in colour, were transferred into a distillation flask. The product of distillation is 44.5 g (50.3 per cent) of tetrahydrothiophen, having a boiling point at 118°–122°C (760 mm Hg), $d_4^{20}$ 0.9998, $n_D^{20}$ 1.5020.

EXAMPLE 6

A steel autoclave described in Example 5 was charged with 72 g (one g-mole) of tetrahydrofuran, 45 g (0.2 g-mole) of phosphorus sulphide $P_2S_5$, and the mixture was kept at 175°C for six hours with stirring. The autoclave was unloaded and the end product was isolated from the reaction mixture as described in Example 5. The yield was 40 g (45.2 per cent) of tetrahydrothiophen having a boiling point of 118°–122°C (760mm Hg), $D_d^{20}$ 1.000, $n_D^{20}$ 1.5015.

EXAMPLE 7

A steel autoclave described in Example 5, was charged with 72 g (one g-mole) of tetrahydrofuran, and 45 g (0.2 g-mole) of phosphorus sulphide $P_2S_5$, and the mixture was kept at 215°C for six hours with stirring. The autoclave was unloaded, and the end product was isolated from it by a method similar to that described in Example 5. The result was 36 g (40.4%) of tetrahydrothiophen having the boiling point of 118°–122°C (760 mm Hg), $d_4^{20}$ 1.000, $n_D^{20}$ 1.5015).

EXAMPLE 8

A rotary steel autoclave having a capacity of one liter, and provided with a pressure gauge and a heat control system, was charged with 72 g (one g-mole) of tetrahydrofuran, 72.6 g (0.33 g-mole) of phosphorus sulphide $P_4S_3$, and the reaction mixture was kept at a temperature of 200°C for six hours with rotation of the autoclave. The autoclave was then cooled to room temperature and the pressure was released. The brown liquid reaction products were transferred into a distillation flask which yielded 10 g of (13.5%) of tetrahydrothiophen having boiling point of from 118°–122°C (760 mm Hg), $d_4^{20}$ 1.000, $n_D^{20}$ 1.5010.

EXAMPLE 9

A rotary steel autoclave of one liter capacity provided with a pressure gauge and a heat control system was charged with 72 g (one g-mole) of tetrahydrofuran, and 52.2 g (0.33 g-mole) of phosphorus sulphide ($P_2S_3$), and the reaction mixture was kept at a temperature of 195°C for six hours with rotation of the autoclave. The autoclave was then cooled to room temperature and the pressure released. The brown liquid reaction product was transferred into a distillation flask and 40 g (45.5%) of tetrahydrothiophen having the boiling point of 118°–122°C was produced (760 mm Hg), $d_4^{20}$ 1.000, $n_D^{20}$ 1.5010).

EXAMPLE 10

A rotary steel autoclave of one-liter capacity, provided with a pressure guage and a heat control system was charged with 72 g (one g-mole) of tetrahydrofuran, and 49.8 g (0.143 g-mole) of phosphorus sulphide $P_4S_7$, and the reaction mixture was kept at a temperature of 200°C for six hours with rotation of the autoclave. The autoclave was then cooled to room temperature and the pressure released. The pale-brown reaction liquid reaction products were then transferred into a distillation flask to separate 17 g (19.3 per cent) of tetrahydrothiophen having a boiling point of 118°–122°C (760 mm Hg), $d_4^{20}$ 1.000, $n_D^{20}$ 1.5010.

What is claimed is:

1. A method for preparing tetrahydrothiophen comprising reacting tetrahydrofuran with a sulphidation agent selected from the group consisting of elementary sulphur and sulphides of phosphorus taken in a stoichiometric ratio of the said substances, at a temperature of from 175° to 215°C, and separating said tetrahydrothiophen from the reaction mixture by distillation at 116°–122°C at atmospheric pressure.

2. A method according to claim 1, in which the reaction between tetrahydrofuran and elementary sulphur is carried out in the presence of red phosphorus taken in the ratio of 0.5-1 g-atom per g-mole of the tetrahydrofuran.

3. A method according to claim 2, in which the reaction between tetrahydrofuran and elementary sulphur in the presence of red phosphorus is carried out at a temperature of from 180°–200°C.

4. A method according to claim 1, wherein additional tetrahydrothiophen is separated from the still bottoms of the reaction mixture by extraction with carbon tetrachloride.

* * * * *